United States Patent
Sidebotham et al.

(10) Patent No.: US 8,597,361 B2
(45) Date of Patent: Dec. 3, 2013

(54) JOINT IMPLANT FIXATION SYSTEM

(75) Inventors: Christopher G. Sidebotham, Mendham, NJ (US); Gregory Thomas Van Der Meulen, Ketchum, ID (US); Randall Lane Acker, Ketchum, ID (US)

(73) Assignee: BioShift, LLC, Ketchum, ID (US)

( * ) Notice: Subject to any disclaimer, the term of this patent is extended or adjusted under 35 U.S.C. 154(b) by 47 days.

(21) Appl. No.: 12/944,331

(22) Filed: Nov. 11, 2010

(65) Prior Publication Data

US 2012/0123553 A1  May 17, 2012

(51) Int. Cl.
*A61F 2/30* (2006.01)

(52) U.S. Cl.
USPC ............... 623/18.11; 623/11.11; 623/16.11

(58) Field of Classification Search
CPC .................................... A61F 2/38; A61F 2/30
USPC ............. 623/11.11, 18.11, 22.11, 16.11
See application file for complete search history.

(56) References Cited

U.S. PATENT DOCUMENTS

| | | | |
|---|---|---|---|
| 5,387,243 A | 2/1995 | Devanathan | |
| 5,876,460 A | 3/1999 | Bloebaum | |
| 6,306,174 B1 * | 10/2001 | Gie et al. | 623/22.42 |
| 7,465,318 B2 | 12/2008 | Sennett et al. | |
| 2002/0049502 A1 * | 4/2002 | DeCarlo et al. | 623/23.27 |
| 2007/0073408 A1 | 3/2007 | Acker et al. | |
| 2007/0233243 A1 | 10/2007 | Sudmann | |
| 2008/0154384 A1 | 6/2008 | Acker et al. | |
| 2008/0183298 A1 * | 7/2008 | McTighe et al. | 623/23.29 |
| 2009/0248158 A1 | 10/2009 | Completo et al. | |
| 2009/0299485 A1 * | 12/2009 | Michelinakis et al. | 623/23.36 |
| 2011/0035012 A1 * | 2/2011 | Linares | 623/18.11 |

FOREIGN PATENT DOCUMENTS

| | | |
|---|---|---|
| EP | 0181586 | 5/1986 |
| WO | WO83/02555 | 8/1983 |
| WO | WO91/16866 | 11/1991 |
| WO | WO98/46169 | 10/1998 |
| WO | WO01/66130 | 9/2001 |
| WO | WO2005/000159 | 1/2005 |
| WO | WO2005/037135 | 4/2005 |
| WO | WO2005/094731 | 10/2005 |
| WO | WO2005/117762 | 12/2005 |
| WO | WO2006/028382 | 3/2006 |
| WO | WO2006/110896 | 10/2006 |
| WO | WO2007/051151 | 5/2007 |
| WO | WO2007/079521 | 7/2007 |
| WO | WO2007/109319 | 9/2007 |

* cited by examiner

*Primary Examiner* — Jason-Dennis Stewart
(74) *Attorney, Agent, or Firm* — Klarquist Sparkman, LLP (57) ABSTRACT

Disclosed are embodiments of an improved joint prosthesis that can provide the option to improve initial stability without removing the implant or altering the preparation. Embodiments of improved joint implant components can comprise one or more expandable, hollow segmented posts. Methods of implant fixation are also disclosed. Disclosed methods can provide the opportunity for establishing initial biologic fixation (bone ingrowth), and can also provide an adjunct fixation through injecting cement down the center of the post if initial stability is not achieved or is questionable.

7 Claims, 8 Drawing Sheets

JOINT IMPLANT FIXATION SYSTEM

FIELD

The disclosed technology relates generally to a joint prosthesis. More specifically, the disclosure relates to a joint prosthesis comprising one or more hollow segmented posts and a method of implanting the same.

BACKGROUND

Joint implants have been designed to replace articular surfaces of many human and animal joints. These implants include replacements for hip, knee, elbow, shoulder, ankle, and other joints. Prosthetic joint implants generally must both replace the bearing surface of the joint for motion and provide some method of fixing the implant to the bone.

Conventional methods of fixing the implant to the bone has been accomplished by two primary methods: bone cement (e.g., PMMA) or bone ingrowth through porous surfaces (biologic fixation). Bone cement is mixed in the operating room and injected into the preparation sites for the implants. The strength of a joint implant's fixation using bone cement is at a maximum shortly after implantation (usually after around 24 hours). Over time, the cement can fatigue and break down, leading to loosening and wear of the implants.

Biologic fixation for prostheses eliminates the need for cement and possibly avoids the long term complications associated with cement fixation. Conventional biologic fixation methods include fixation through a porous surface created by layers of sintered beads, plasma sprayed surface, titanium wire, and other micro and macro surfaces providing for a mechanical lock with bone. Bone ingrowth within the first 10-12 weeks after surgery essentially determines whether the implant will be stable long term. In order to be successful, the porous surfaces or macro surfaces must be well designed for bone attachment and the implant must be very stable during this early post-operative time period. If there is too much motion between the implant and the bone, a fibrous tissue interface will occur rather than bone ingrowth. Should that happen, the long term success will be in jeopardy as loosening due to pain and micromotion can create a need for revision.

For stability to be consistently achieved during the preparation of the bones for the implant insertion, very precise instruments and very consistent surgical techniques are required. In many cases this cannot consistently be achieved due to many variables including surgeon error, worn instruments, and patient issues. In some cases, discovery of a problem may come after insertion of the implant. For example, during surgery, after the bones have been prepared for biologic fixation, trial implants placed and evaluated, and the final implants selected and inserted into their corresponding preparations, the surgeon may discover that the patient's joint is not suitable for biologic fixation.

However, addressing these problems usually requires removing the implant and/or attempting further preparation to the bony beds. Different bone preparation techniques are required for cement fixation, and thus switching from one method to the other mid-surgery typically requires removing the implant and essentially starting over from the beginning. Further, conventional joint implants are subject to post-operative loosening due to, for example, inadequate stability due to initial patient activity. There thus remains a need for an improved joint implant that can address these and other disadvantages in the prior art joint implants and implantation methods.

SUMMARY

Disclosed are embodiments of an improved joint prosthesis that can provide the option to improve initial stability without removing the implant or altering the preparation. Embodiments of joint implant components can include one or more hollow segmented posts positioned on one or more bone fixation surfaces. The segmented posts can include a central opening configured to receive cement for initial stability of the implant. Cement can be injected at the time of implantation, at a time after implantation (e.g., during later revision surgery), or not at all. The segmented posts can be expandable to form or increase a press fit within a bore or hole drilled in the patient's bone, thereby further increasing stability of the implant in some embodiments.

One embodiment of a joint implant component comprises a bone-engaging or bone fixation surface configured to engage with a patient's bone and at least one post (e.g., a fixation post) protruding outwardly from the bone fixation surface. The post can comprise at least two segments, each segment being separated by a gap, and the segments can define a central opening through the centers of said segments. Thus, the post can be a hollow segmented post. The segments of each fixation post can be substantially aligned with one another.

In some embodiments, the at least one post comprises at least a first and second post protruding from the bone fixation surface, the first and second posts being positioned on opposite portions of the joint implant from each other. The first and second posts can be positioned substantially parallel to one another in some specific embodiments. At least one post can be positioned tangentially to the bone fixation surface, substantially parallel to a longitudinal axis of the joint implant, and/or transversely to a major axis of the joint implant. The segments of each post can be positioned relative to one another such that they are configured to receive a cement injection needle within the central opening through the segments.

In some embodiments, the joint implant can comprise at least a first implant member and a second implant member, the first and second implant members being configured to articulate with each other (e.g., the joint implant can be a bicompartmental joint implant). Unicompartmental and tri-compartmental joint implants are also disclosed. In embodiments with more than one implant component, the first implant member can comprise a first bone fixation surface and the second implant member can comprise a second bone fixation surface, and both the first and second bone fixation surfaces can comprise at least one post protruding from said first and second bone fixation surfaces. In some embodiments, each segment of the fixation post is substantially C-shaped.

Some embodiments of joint prostheses include porous surfaces. For example, at least part of one fixation post can include a porous surface (e.g., a porous coating). In some embodiments, at least a portion of the bone fixation surface comprises a porous coating. For example, portions of the bone fixation surface between fixation posts can comprise a porous coating or treatment.

The fixation posts can be configured to be expandable from a first position to a second position, wherein the diameter of the central opening is increased in the second position with respect to the first position. Such expansion can contribute to initial implant stability within a patient's bone by increasing the press fit between the post and a hole drilled in the patient's bone.

Disclosed concepts can be applied to any type of joint implant prosthesis. For example, any of the following specific implant components can be provided with one or more hollow, expandable fixation posts according to the present disclosure: an elbow implant component, an acetabular cup, a femoral hip stem, a shoulder humeral stem, a femoral knee implant component, a tibial knee implant component, or an ankle tibial implant component. Of course this list is non-exhaustive, and any other type of joint implant or implant component can include one or more fixation posts according to the present disclosure.

One embodiment of a joint implant component comprises a post portion configured to engage with a patient's bone, the post portion comprising a plurality of segments positioned around the circumference of the post portion and spaced apart by a plurality of longitudinal slits extending along at least a portion of the length of the post portion. The joint implant component can also comprise a taper portion coupled to the post portion, wherein the post portion and taper portion are arranged such that a longitudinal central opening extends through the post portion and taper portion. The segments of the post portion can be expandable from a first configuration to an expanded configuration. The diameter of the central opening can be increased in the expanded configuration with respect to the first configuration.

The segments can be positioned relative to one another such that they are configured to receive a cement injection needle within the central opening. In some embodiments, at least a part of the post portion can have a porous surface. One specific embodiment of a joint implant component comprises a femoral hip stem.

In some embodiments, the taper portion can comprise internal threads within the central opening. Such threads can be configured to engage with a threaded expansion tool that can be used to expand the post portion from the first configuration to the expanded configuration.

Some embodiments can comprise a curved annular portion positioned between the taper portion and the post portion, wherein the curved annular portion is configured to engage with a surface of a patient's bone.

Methods of implant fixation are also disclosed. Disclosed methods can provide the opportunity for establishing initial biologic fixation (bone ingrowth), and can also provide an adjunct fixation through injecting cement down the center of the post if initial stability is not achieved or is questionable.

One method of replacing at least part of a patient's joint with one or more joint implant components can comprise preparing the implant site to receive the one or more joint implant components and implanting the joint prosthesis wherein at least a portion of the implant component is positioned at least partially within a hole drilled into a patient's bone, wherein the joint implant component comprises a bone fixation surface and at least one segmented post protruding from the bone fixation surface, and wherein the post comprises at least two segments, each segment being separated by a gap, and wherein the segments define a central opening through the center of said segments.

Some methods can comprise expanding the at least one segmented post from a first configuration to a second configuration, wherein the diameter of the central opening is increased in the second configuration with respect to the first configuration. In some embodiments, expanding the at least one segmented post can comprise drawing a tapered expansion tool through at least part of the segmented post.

Some methods can comprise evaluating whether biologic fixation is suitable as the sole fixation method at the time of implantation, and injecting cement into the central opening. For example, an implant site can be prepared for biologic fixation, and disclosed embodiments of joint implant components can be implanted at the site. If it is determined that biologic fixation is not suitable for that patient, conventional methods would require removal of the implant, and re-preparation of the implant site for cement fixation. Disclosed methods, on the other hand, can allow for use of bone cement without requiring removal of the implant component or further alteration of the implant site.

In some methods, the joint replacement can be completed and a follow up evaluation some time after completion of the joint replacement can be conducted to determine whether the joint prosthesis is sufficiently stable. Cement can be injected into the central opening, for example, at a time after initial implantation. For example, if a follow-up evaluation reveals that bone ingrowth has been insufficient for long-term implant stability, revision surgery can be conducted to increase fixation of the implant within the patient's bone. In some embodiments, cement can be injected into one or more of the hollow segmented posts. In some embodiments, fibrous growth may need to be removed from the fixation posts before cement can be injected.

The foregoing and other objects, features, and advantages of the invention will become more apparent from the following detailed description, which proceeds with reference to the accompanying figures.

DETAILED DESCRIPTION

As used in this application and in the claims, the singular forms "a," "an," and "the" include the plural forms unless the context clearly dictates otherwise. Additionally, the term "includes" means "comprises." Although the operations of exemplary embodiments of the disclosed method may be described in a particular, sequential order for convenient presentation, it should be understood that the disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed herein. Moreover, for the sake of simplicity, the attached figures may not show the various ways in which the disclosed system, method, and apparatus can be used in combination with other systems, methods, and apparatuses.

To address the problems discussed above with conventional joint prostheses, the present disclosure concerns a joint prosthesis designed to facilitate bone ingrowth (e.g., designed to be secured within a patient's joint via biologic fixation), and yet is also designed to facilitate cement fixation, either at the time of initial implantation, or some time after implantation. Disclosed joint prostheses and methods enable a surgeon to prepare a treatment site for biologic fixation, insert a joint prosthesis, and evaluate whether biologic fixation seems appropriate for the particular patient. If the surgeon determines at this stage in surgery that cement fixation is necessary, a surgeon using a conventional joint prosthesis would be required to remove the prosthesis, re-prepare the treatment site, and begin again. On the other hand, a surgeon using one of the presently disclosed joint prostheses and methods would advantageously be able to inject cement into the joint prosthesis without needing to remove the implant or alter the bone preparation already completed. In this manner, disclosed embodiments of joint prostheses can allow a surgeon to adapt to individual patient needs, while potentially shortening the time required for surgery.

Disclosed embodiments of joint prostheses and methods of using the same can be used with both human and animal joints. Additionally, the disclosed principles can be applied to any joint prosthesis and are not limited to the specific examples described herein. Unicompartmental, bicompartmental, and tricompartmental joint prostheses can all be designed to include one or more hollow segmented posts, as will be described further.

Figures 1, 2:
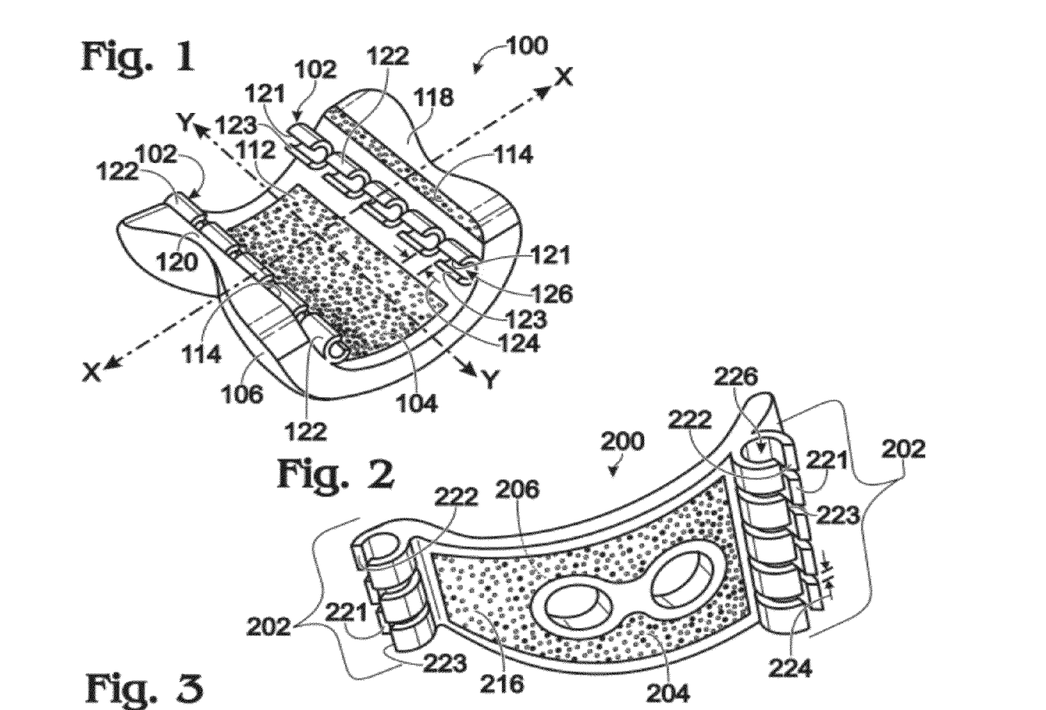
FIG. 1 is a perspective view of one component of a joint prosthesis having hollow segmented posts according to the present disclosure.
FIG. 2 is a perspective view of a second component of a joint prosthesis having hollow segmented posts.
Figure 3:
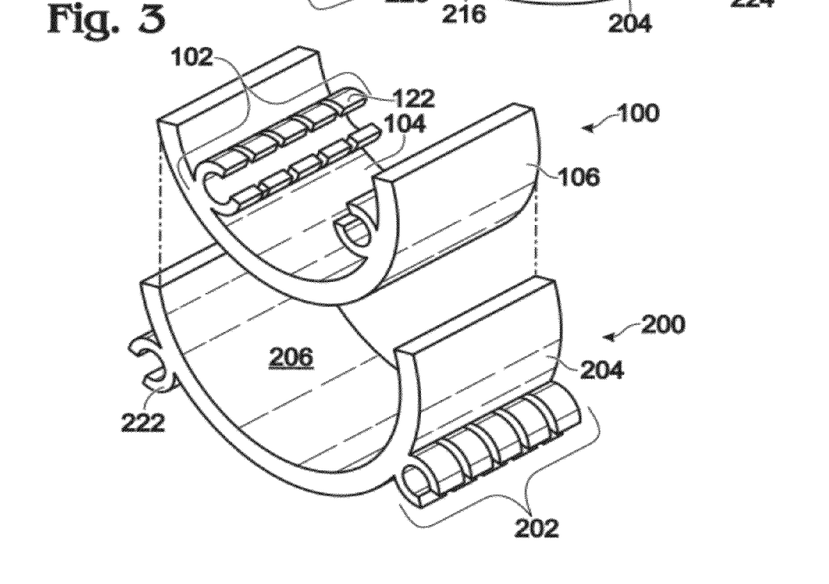
FIG. 3 is an exploded view of a simplified schematic representation of an elbow joint prosthesis.

By way of illustration, one embodiment of a joint prosthesis in the form of a bicompartmental elbow implant is shown in FIGS. 1-4. FIG. 1 shows one embodiment of a humeral component 100, and FIG. 2 shows one embodiment of a radioulnar component 200. As shown in FIG. 3 (which is a simplified representation), the humeral component 100 and the radioulnar component 200 can be configured to interact with one another to form an articulating prosthetic elbow joint 400, which is shown implanted in FIG. 4.

In the example shown in FIGS. 1-4, the humeral component 100 and the radioulnar component 200 each includes two fixation posts 102, 202 protruding outwardly from respective bone-engaging surfaces 104, 204. While FIGS. 1-4 illustrate each joint prosthesis component 100, 200, having two fixation posts, in alternative embodiments, each component 100, 200 may have more or fewer fixation posts. For example, in one alternative embodiment, a first joint prosthesis component can comprise one or more fixation posts, while a second joint prosthesis component can be provided without any fixation posts. In another specific example, a first joint component can comprise one fixation post and a second joint component can comprise two or more fixation posts. A suitable number of fixation posts can be determined based on the particular joint application and can vary for different designs of joint prostheses.

Figures 4, 5, 6:
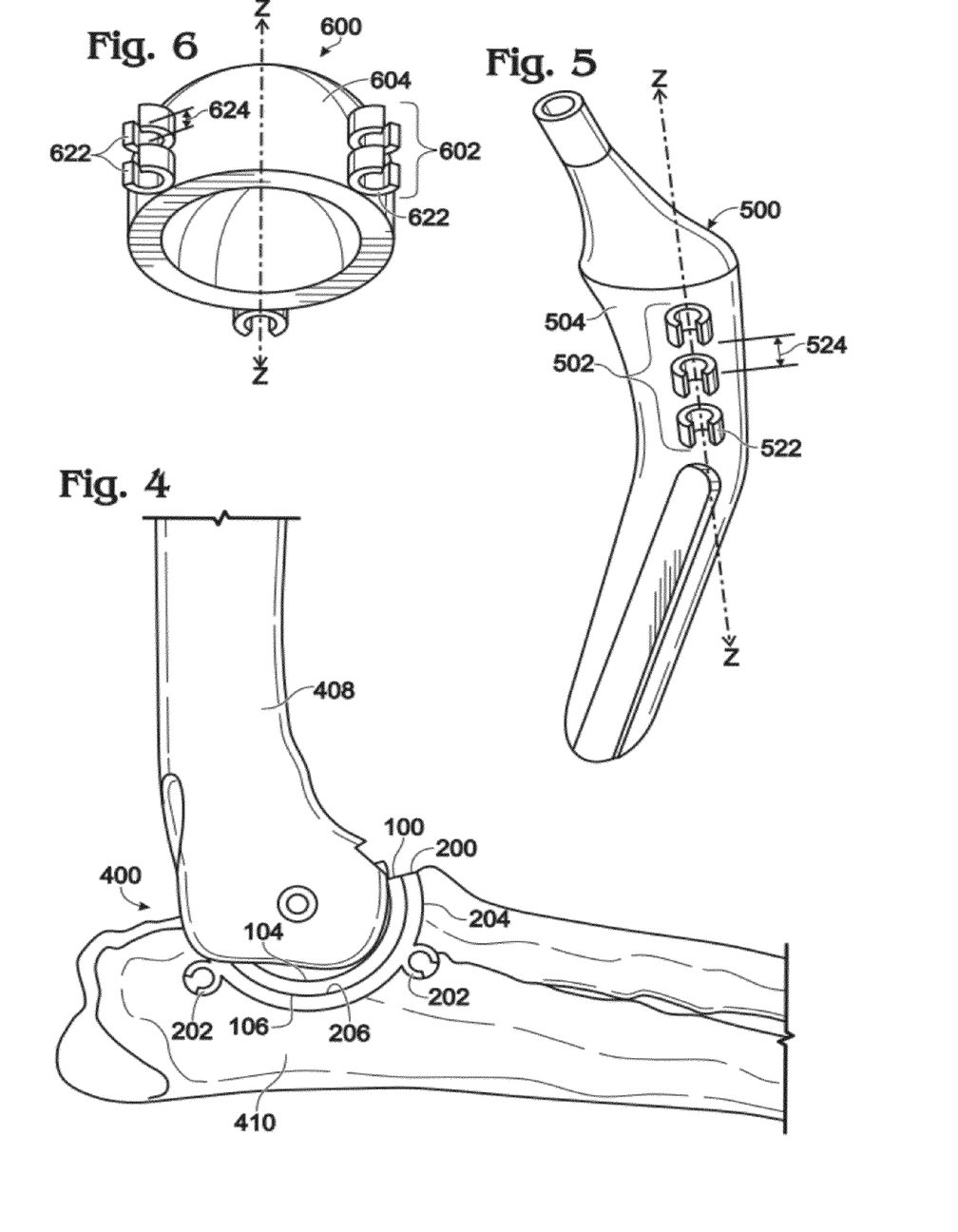
FIG. 4 is a side elevation view of a joint prosthesis implanted in a subject's joint.
FIG. 5 is a perspective view of an alternative joint prosthesis according to the present disclosure.
FIG. 6 is a perspective view of an alternative joint prosthesis according to the present disclosure.

Returning to FIGS. 1-4, the humeral component 100 can comprise a bone-engaging surface 104 opposite an articulating surface 106. The radioulnar component 200 can comprise a bone-engaging surface 204 opposite an articulating surface 206. As shown in FIGS. 3-4, the joint prosthesis 400 is designed such that, when implanted, the articulating surface 106 of the humeral component 100 and the articulating surface 206 of the radioulnar component 200 interact with one another such that the humeral component 100 can move with respect to the radioulnar component (e.g., the articulating surfaces 106, 206 slide back and forth against one another), thereby providing joint movement. The interaction of the humeral component 100 and the radioulnar component 200 is shown in FIG. 3, in exploded view.

The bone-engaging surfaces 104, 204 each can engage with a bone at the implantation site. In the particular example shown in FIGS. 1-4 (and as best seen in FIG. 4), the bone-engaging surface 104 engages with a humerus 408 and the bone-engaging surface 204 engages with the radius and/or ulna 410. In other embodiments (e.g., with other types of joint implants according to the present disclosure), the bone engaging surfaces can engage with different bones, as determined by the particular joint the joint implant is designed to replace.

Figure 14:
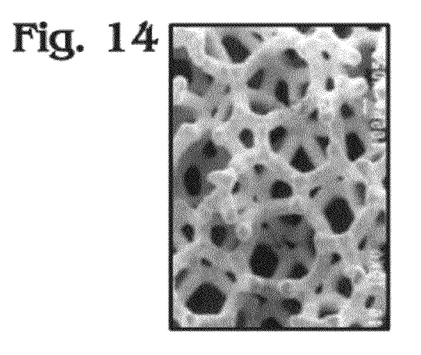
FIG. 14 is a black and white SEM photo of a porous surface having a tantalum structure with interconnected porosity.

The bone-engaging surfaces 104, 204 can comprise one or more portions configured to encourage bone growth. For example, central portion 112 and edge portions 114 of the humeral component 100, as well as portion 216 of the radioulnar component 200 can comprise a porous coating. In some embodiments, only a portion of the bone-engaging surfaces 104, 204 is treated with such porous coatings. In some embodiments, substantially all of the bone-engaging surfaces 104, 204 are treated with one or more porous coatings. In some embodiments, at least a portion of the surfaces of one or more fixation posts 102, 202 can include one or more porous coatings. Examples of suitable porous coatings are shown in FIGS. 11-14 and include a plasma spray porous surface (FIG. 11), a sintered bead porous surface (FIG. 12), a fiber metal porous surface (FIG. 13), and a porous tantalum structure with interconnected porosity (FIG. 14).

One or more fixation posts 102, 202 can be positioned on the bone-engaging surfaces 104, 204 of joint components 100, 200. Humeral component 100 can include two fixation posts 102 positioned on the bone-engaging surface 104. In some embodiments, as shown in FIG. 1, the two fixation posts 102 can be positioned substantially parallel to one another, adjacent opposite ends 118, 120 of the humeral component 100. The posts 102, 202 can protrude outwardly from the bone-engaging surface 104, 204 and each can be formed of at least two substantially aligned segments 122, 222, respectively, separated from each other along the bone-engaging surface 104, 204 by respective gaps 124, 224.

Each segment 122, 222 can be a partially closed segment having two free ends. For example, each segment 122 can have free ends 121, 123 and each segment 222 can have free ends 221, 223. Each segment 122, 222 can be, for example, a C-shaped structure integrally formed with or coupled to the bone-engaging surface 104, 204 (e.g., by welding). In other embodiments, each segment can be, for example, a substantially elliptical, oval, circular (e.g., O-shaped with a small gap between two free ends), angular, triangular, square, rectangular, V-shaped, or D-shaped structure coupled to the bone-engaging surface of a joint implant component. Other shapes can also be suitable.

The segments 122, 222 can be substantially aligned with one another so as to form respective central openings 126, 226 through the centers of the segments 122, 222. Each central opening 126, 226 can be, for example, a substantially cylindrical opening. Each central opening 126, 226 is discontinuous due to the gaps 124, 224 between adjacent segments 122, 222, but each opening 126, 226 nonetheless can be configured to receive a cylindrical object such as a cement injection needle. The fixation posts 102, 202 and central openings 126, 226 can also be configured to receive ingrowing bone. For example, bone can grow into the segments 122, 222 between the free ends and/or between the segments (e.g., in gaps 124, 224). Thus, the humeral and radioulnar components 100, 200 and their fixation posts 102, 202 can be configured for biologic fixation and/or for cement fixation.

The fixation posts 102, 202 can be positioned tangential to the bone-engaging surface 104, 204 in some embodiments. The orientation of the fixation posts 102 can be at least partially defined with respect to a major axis X and a minor axis Y. Generally, major axis X corresponds to the longest dimension of the joint component, and the minor axis Y is perpendicular to the major axis X. In the case of the humeral component 100 of FIG. 1, the overall cross-sectional shape of the component 100 can be substantially half of an ellipse (e.g., when viewed from the side), and the major axis X passes through foci proximate to opposite ends 118, 120, as well as the center of the implant component 100. As in FIG. 1, the fixation posts 102 can be positioned such that they cross (e.g., are transverse to) the major axis X. In FIG. 1, the fixation posts 102 are positioned substantially parallel to the minor axis Y (e.g., substantially perpendicular to the major axis X). In other embodiments, the fixation posts can be positioned to cross the major axis X at a non-perpendicular angle to the major axis X.

Fixation posts 102, 202 can be expandable from a first position to a second position, wherein the diameter of the central opening is increased in the second position with respect to the first position, as will be described further below in connection with FIGS. 16-17. One or more segments 122, 222 of the respective fixation posts 102, 202 can be provided with internal threads (e.g., the surface of the segments 122 facing the central opening 126 can be threaded).

FIGS. 5-10 show alternative examples of embodiments of joint implants (or joint implant components) that include one or more fixation posts in various positions on the joint implant (e.g., on the bone-engaging surface of one or more joint implant components). These embodiments are exemplary only, and many other configurations and implant types are possible.

FIG. 5 shows a prosthetic femoral hip stem 500 having a longitudinal axis Z. The femoral hip stem 500 can include one or more fixation posts 502 positioned on and protruding outwardly from a bone-engaging surface 504. The fixation posts 502 can be positioned substantially parallel to the longitudinal axis Z in some embodiments. While only one fixation post 502 is visible in FIG. 5, the femoral hip stem 500 can include one or more additional fixation posts 502 spaced around the implant.

The fixation post 502 can include at least two substantially aligned segments 522 (e.g., C-shaped segments) separated from each other along the bone-engaging surface 504 by a gap 524. The segments 522 of a fixation post 502 can define a central opening through the centers of the segments 522. While the embodiment shown in FIG. 5 includes three substantially aligned segments 522, other embodiments can include one or more fixation posts having more or fewer segments. As with all described embodiments, at least a portion of the joint implant 500 (e.g., the bone-engaging surface) and/or at least a portion of the one or more fixation posts 502 can be porous. For example, at least a portion of the joint implant 500 and/or at least a portion of the fixation post 502 can be treated with a porous coating, such as the porous coatings shown in FIGS. 11-14. Fixation post 502 can be expandable, in accordance with FIGS. 16-17.

FIG. 6 shows one embodiment of an acetabular cup 600 having a longitudinal axis Z. The acetabular cup 600 can include one or more fixation posts 602 positioned on a bone-engaging surface 604. The fixation posts 602 can be positioned substantially parallel to the longitudinal axis Z in some embodiments. While two fixation posts 602 are visible in FIG. 6, the acetabular cup 600 can include one or more additional fixation posts 602 spaced around the implant. The fixation posts 602 can each include at least two substantially aligned segments 622 (e.g., C-shaped segments) separated from each other along the bone-engaging surface 604 by a gap 624. The segments 622 of a fixation post 602 can define a central opening through the segments 622. While the embodiment shown in FIG. 6 includes three substantially aligned segments 622 forming each fixation post 602, other embodiments can include one or more fixation posts having more or fewer segments. Fixation posts 602 can be expandable, in accordance with FIGS. 16-17.

Figure 7:
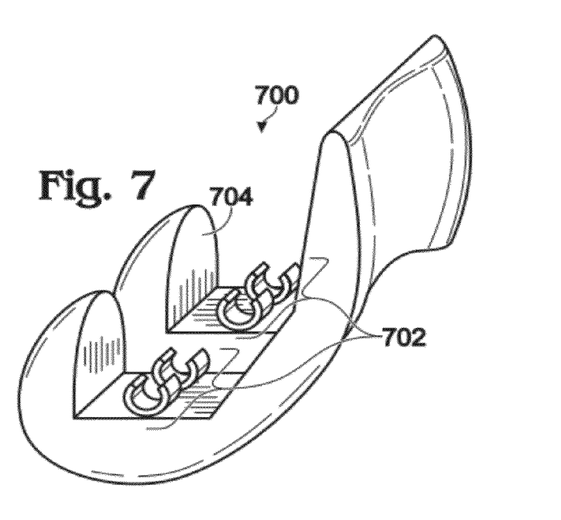
FIG. 7 is a perspective view of an alternative joint prosthesis according to the present disclosure.
Figure 8:
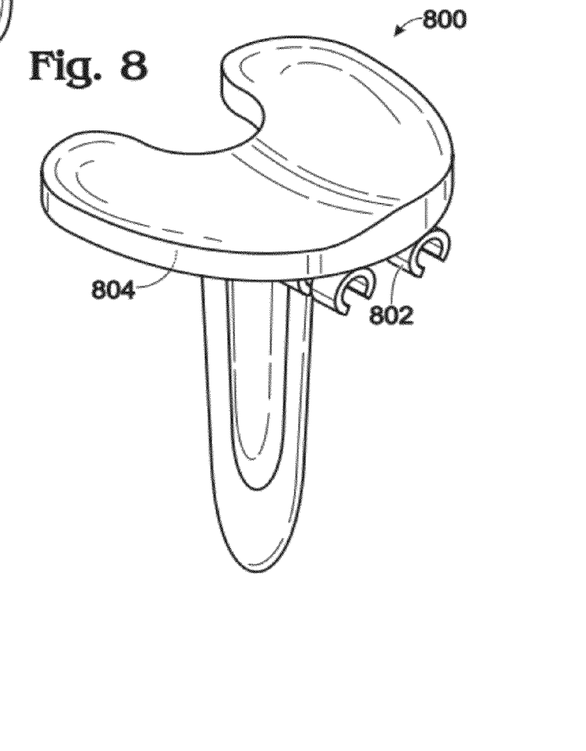
FIG. 8 is a perspective view of an alternative joint prosthesis according to the present disclosure.

FIG. 7 shows one embodiment of a femoral knee implant 700 that can interact with the knee tibial implant 800 of FIG. 8 to form a complete prosthetic knee implant. Femoral knee implant 700 can include a bone-engaging surface 704 configured to engage with a patient's femur and one or more fixation posts 702 protruding from the bone-engaging surface 704. Similarly, the knee tibial implant 800 can include one or more fixation posts 802 protruding from a bone-engaging surface 804 configured to engage with a patient's tibia. The fixation posts 702, 802 can each include at least two substantially aligned segments (e.g., C-shaped segments) separated from each other along the bone-engaging surface 704, 804 by a gap. The segments of a fixation post 702, 802 can define a central opening through the segments. Fixation posts 702, 802 can be expandable, in accordance with FIGS. 16-17.

Figure 9:
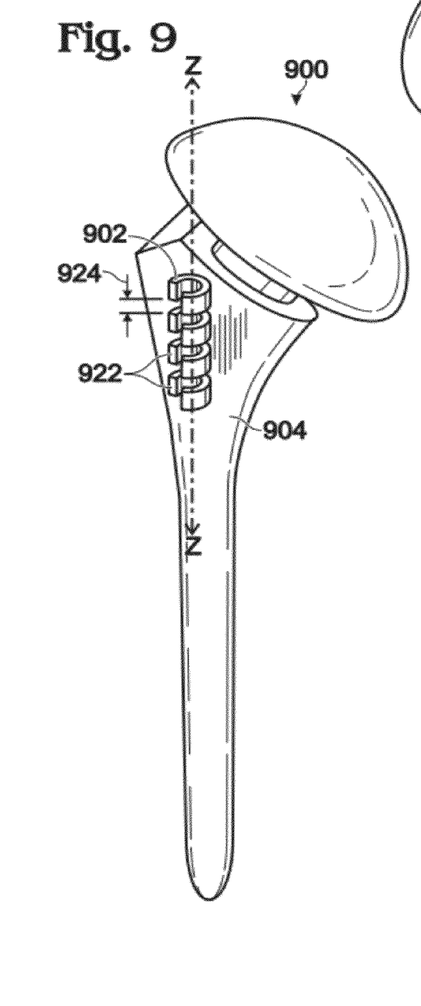
FIG. 9 is a perspective view of an alternative joint prosthesis according to the present disclosure.

FIG. 9 shows a prosthetic shoulder humeral stem 900 having a longitudinal axis Z. The shoulder humeral stem 900 can include one or more fixation posts 902 positioned on and protruding from a bone-engaging surface 904 configured to engage with a patient's bone (e.g., the humerus). The fixation posts 902 can be positioned substantially parallel to the longitudinal axis Z in some embodiments. While only one fixation post 902 is visible in FIG. 9, the shoulder humeral stem 900 can include one or more additional fixation posts 902 spaced around the implant. The fixation post 902 can include at least two substantially aligned segments 922 (e.g., C-shaped segments) separated from each other along the bone-engaging surface 904 by a gap 924. While the embodiment shown in FIG. 9 includes four substantially aligned segments 922, other embodiments can include one or more fixation posts having more or fewer segments. The segments 922 of a fixation post can be arranged to define a central opening through the segments 922. Fixation posts 902 can be expandable, in accordance with FIGS. 16-17.

Figure 10:
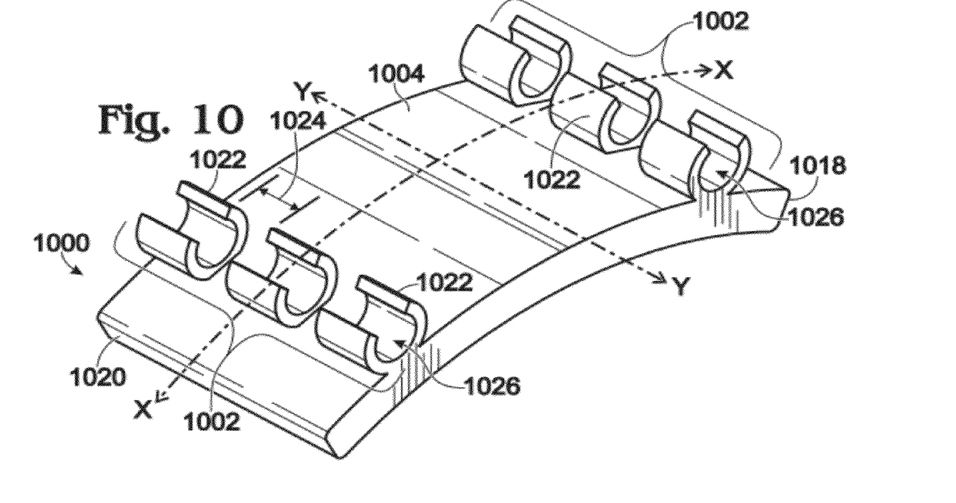
FIG. 10 is a perspective view of an alternative joint prosthesis according to the present disclosure.
Figure 11:
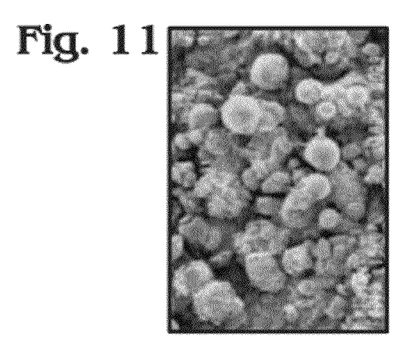
FIG. 11 is a black and white scanning electron micrograph (SEM) photo of a plasma spray porous surface.
Figure 12:
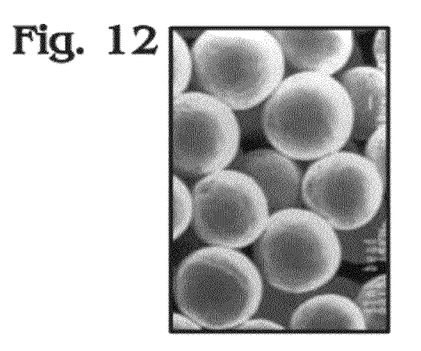
FIG. 12 is a black and white SEM photo of a sintered bead porous surface.
Figure 13:
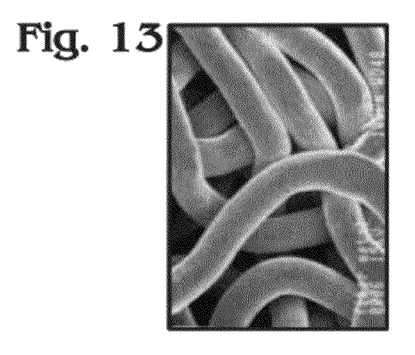
FIG. 13 is a black and white SEM photo of a fiber metal porous surface.

FIG. 10 shows a prosthetic ankle tibial implant 1000 having a bone-engaging surface 1004 configured to engage with a patient's bone (e.g., the tibia). The bone-engaging surface 1004 can include one or more fixation posts (e.g., hollow, segmented posts) 1002 protruding outwardly from the bone-engaging surface 1004. The fixation posts 1002 can be formed from two or more adjacent, substantially aligned segments 1022 (e.g., C-shaped segments) separated from each other along the bone-engaging surface 1004 by a gap 1024. Fixation posts 1002 (e.g., segments 1022 of the fixation posts 1002) can be expandable, in accordance with FIGS. 16-17.

As shown in FIG. 10, a first fixation post 1002 can be positioned near a first edge portion 1018 and a second fixation post 1002 can be positioned near a second edge portion 1020 opposite the first edge portion 1018 of the ankle tibial implant 1000. A major axis X and a minor axis Y can be associated with the ankle tibial implant 1000, and one or more of the fixation posts can be positioned to cross (e.g., be positioned transverse to) the major axis X. In the specific embodiment shown in FIG. 10, the fixation posts are positioned substantially perpendicular to the major axis X, but other arrangements are also suitable. For example, fixation posts can be positioned at a non-perpendicular angle to the major axis X in some embodiments.

Fixation posts 1002 each comprise three substantially aligned segments 1022, but in alternative embodiments, the fixation posts 1002 can comprise more or fewer segments. The fixation posts 1002 can be configured such that the interior of the segments 1022 forms a central opening 1026 (e.g., a substantially cylindrical opening 1026) that can be configured to receive a cylindrical object (e.g., a bone cement injection needle) and/or biologic tissue (e.g., bone ingrowth from the patient's bone). The fixation posts 1002 can be positioned tangentially to the bone-engaging surface 1004, with the open portions of the segments 1022 facing outward (e.g., facing away from the bone-engaging surface 1004). Such arrangements of the segments 1022 of the fixation posts 1002 can facilitate expansion of the fixation posts 1002, as will be described further below.

Any of the disclosed embodiments of joint implants having one or more hollow, segmented fixation posts can be configured such that the fixation posts are expandable from an original position to an expanded position. For example, FIG. 16 shows a schematic elevation view of one segment 1622 of a fixation post positioned on a joint implant component 1600, with the fixation post in its original position within a hole 1628 drilled into a patient's bone 1630.

Figure 17:
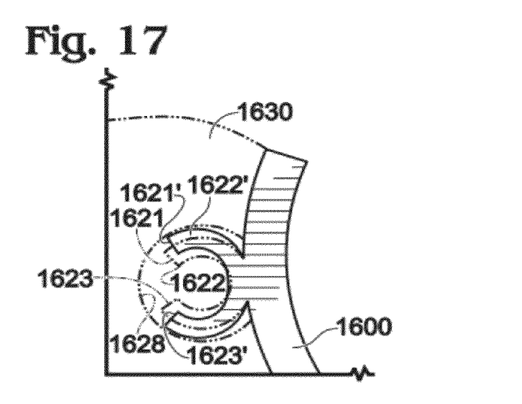
FIG. 17 is a side elevation view of a hollow segmented post in an expanded configuration.

FIG. 17 shows a schematic elevation view of the segment 1622 of a fixation post in its expanded configuration 1622' within the hole 1628 drilled into a patient's bone 1630. The original position of segment 1622 is shown in FIG. 17 in phantom, for reference. In expanding the segment 1622', the free ends 1621', 1623' can be moved farther apart from one another than the free ends 1621, 1623 were in the original configuration. Such expansion of the fixation post segments generally involves permanent expansion (e.g., permanent deformation) as opposed to elastic deformation. In this manner, once the segments 1622 are expanded to an expanded configuration, they generally do not return to their original positions.

Figure 16:
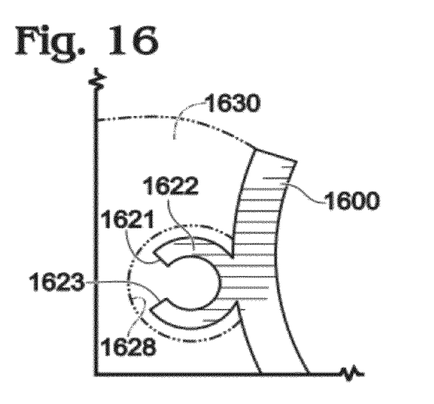
FIG. 16 is a side elevation view of a hollow segmented post in an unexpanded configuration.

As shown in FIGS. 16-17, by expanding a fixation post (e.g., by expanding some or all of the segments 1622 that form a fixation post), one or more of the expanded segments 1622' can engage with the patient's bone 1630 (e.g., the surface of the bone 1630 facing the hole 1628) such as to provide frictional engagement between the segment 1622' and the bone 1630. Such frictional engagement can provide further stability for the joint implant component 1600. Thus, any of the disclosed embodiments of fixation posts can increase stability (e.g., fixation) of the joint implant and/or joint implant components.

While FIG. 16 shows a visible gap between the segment 1622 and the hole 1628, the hole 1628 is generally drilled to provide a press fit engagement with the fixation post, and FIG. 16 shows a gap for clarity, and to emphasize the expansion of the segment 1622. Thus, expansion of the segments 1622 can increase the strength of the fixation of the joint implant component 1600 to the bone 1630.

Figure 18:
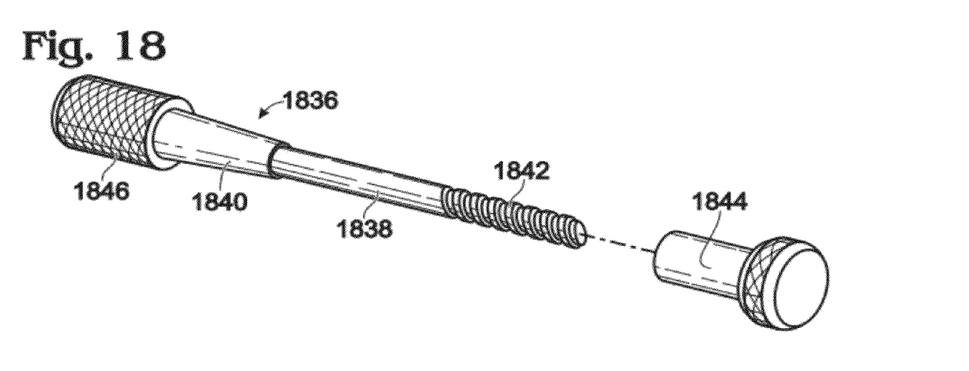
FIG. 18 is a perspective view of one example of an expansion tool that can be used to expand a hollow segmented post from an unexpanded to an expanded configuration.

FIG. 18 shows one embodiment of an expansion tool 1836 that can be used to expand segments of a fixation post, such as shown in FIGS. 16-17. Expansion tool 1836 can comprise a central portion 1838, an enlarged tapered portion 1840, and a threaded portion 1842. Threaded portion 1842 can be configured to engage with, for example, a thumb screw 1844. Threaded portion 1842 and central portion 1838 can be configured to fit within the central opening of a fixation post. A handle portion 1846 can be provided at one end of the expansion tool 1836, opposite the threaded portion 1842. The expansion tool 1836 can be long enough that the handle portion 1846 can extend out one end of a fixation post, while at least a portion of the threaded portion 1842 can extend out the opposite end of the fixation post. A thumb screw 1844 or other device can be used to engage with the threaded portion 1842 and turn the expansion tool 1836 so as to pull it at least partially into the central opening of a fixation post. As the expansion tool 1836 is pulled into a fixation post, the enlarged tapered portion 1840 can cause the segments of the fixation post to expand, as the enlarged tapered portion is pulled into the segments, forcing them to expand outwardly. One or more segments of a fixation post can be expanded in this manner, and then the expansion tool 1836 can be removed from the fixation post. If desired, the expansion tool 1836 can be inserted in the opposite end of the fixation post to expand one or more segments of the other end of the fixation post. In this manner, one or more the segments on either end of the fixation post can be expanded. In some embodiments, an expansion tool can expand all of the segments of a fixation post.

Any other suitable tool or device can also be used to expand one or more segments of one or more fixation posts on a joint implant component in a similar or other fashion. For example, in one alternative embodiment, the segments can be provided with internal threads that can engage a tapered tool, without the need for a separate thumb screw device as described above. In other embodiments, a tapered tool can be inserted, such as by a hammer, into the fixation post in order to expand one or more segments.

Figures 19, 20:
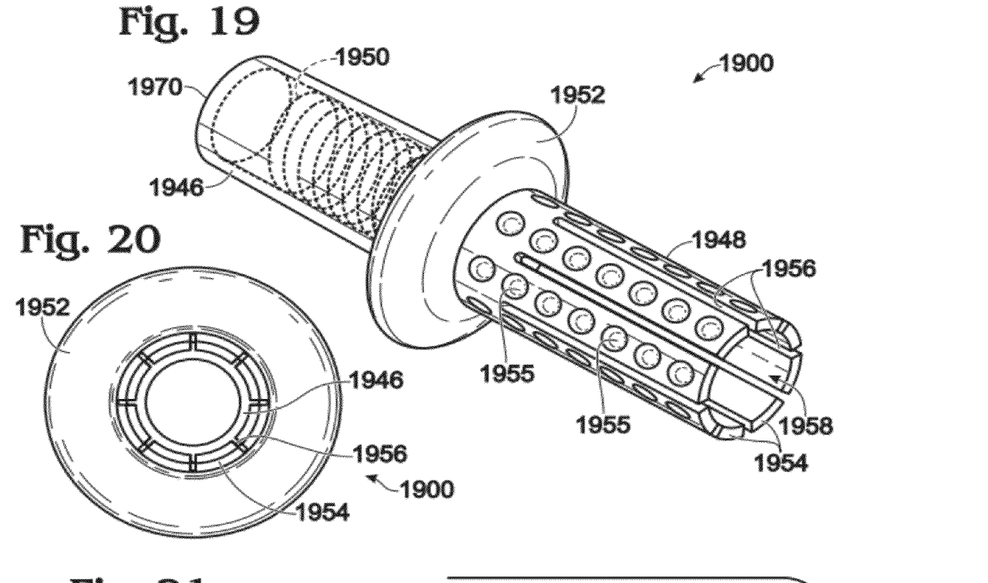
FIG. 19 is a perspective view of another embodiment of a joint prosthesis according to the present disclosure.
FIG. 20 is a top plan view of the joint prosthesis of FIG. 19.

FIGS. 19-20 show another embodiment of a joint implant component 1900 comprising one or more hollow segmented fixation posts. Implant component 1900 is particularly adapted to be a femoral hip implant for example purposes, but the described concepts can be applied to other types of joint implants as well. While the joint implant embodiments shown in FIGS. 1-10 generally include fixation posts that can be inserted and expanded in a hole tangential to the implant surface, the embodiment of FIGS. 19-20 provide a joint implant having an expandable fixation post that can be inserted into a hole that is perpendicular to the osteotomy surface, or inserted into a blind- or through-hole.

Joint implant component 1900 can include a taper portion 1946 coupled to a post portion 1948, both being substantially parallel to the longitudinal axis of the implant component 1900. The post portion 1948 is at least partially inserted in a patient's bone (and thus is configured to engage with a patient's bone), and at least a portion of the taper portion 1946 rests outside of the bone. Taper portion 1946 can include internal threads 1950 for, by way of example, receiving another joint implant component (e.g., a metal femoral head configured to engage with an acetabulum) and/or for engaging with an expansion tool. Implant component 1900 can include a curved annular portion 1952 positioned between the taper portion 1946 and the post portion 1948. The curved annular portion 1952 can be configured as a bone-engaging surface configured to engage with a patient's bone. The post portion 1948 can protrude outwardly from the curved annular portion 1952.

Post portion 1948 can include a plurality of longitudinal slits 1956 positioned between adjacent segments 1954 (e.g., at least a portion of each of the segments 1954 is separated from an adjacent segment 1954 by a gap 1956). The longitudinal slits 1956 can extend along at least a portion of the length of the post portion 1948. The longitudinal slits 1956 can also provide additional surfaces for bone ingrowth (e.g., bone can grow through the slits 1956 and into the central opening 1958).

In this manner, the segments 1954 can be positioned around the circumference of the post portion 1948 such that the segments 1954 can define a central opening 1958 through the center of the segments 1954. The central opening 1958 can be configured to receive, for example, a cement injection needle. Longitudinal central opening 1958 can extend through the post portion 1948, taper portion 1946, and curved annular portion 1952. However, the central opening 1958 need not have a constant diameter through the entire implant component 1900. For example, the diameter of the central opening 1958 can be larger within the taper portion 1946 than it is within the post portion 1948.

One or more portions of the joint implant component 1900 can comprise a porous surface, such as one or more of the porous surfaces shown in FIGS. 11-14. For example, one or more portions of the joint implant component 1900 can comprise a plasma spray porous surface (FIG. 11), a sintered bead porous surface (FIG. 12), a fiber metal porous surface (FIG. 13), and/or a porous tantalum structure with interconnected porosity (FIG. 14). Such portions of porous surface coatings or treatments can increase bone ingrowth in and around the segments 1954 of the post portion 1948. For example, at least a portion of the outer, bone-engaging surfaces of segments 1954 can comprise a porous coating. In some embodiments, at least a portion of the inner surface of the segment 1954 (e.g., facing the central opening 1958) can comprise a porous coating. In some embodiments, each segment 1954 can comprise one or more recesses 1955. Such recesses 1955 can be configured to encourage bone growth in and around the post portion 1948 of the implant component 1900.

The segments 1954 can be arranged around the circumference of the post portion 1948, and can be configured to expand radially outward to increase the diameter of a central opening 1958 of the joint implant component 1900 (e.g., by increasing the space between adjacent segments 1954).

Figure 21:
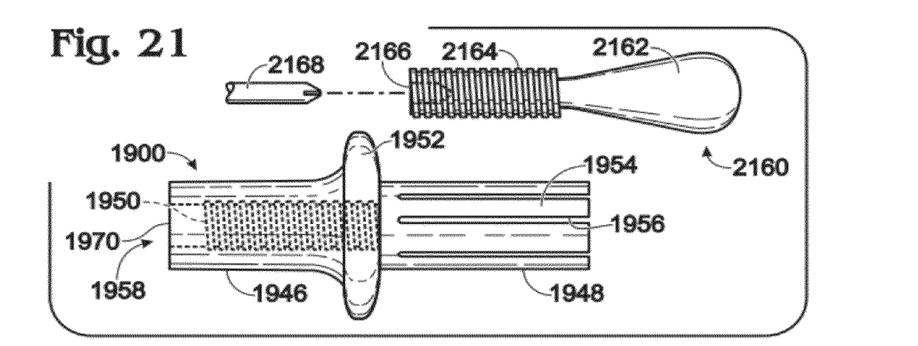
FIG. 21 shows an elevation view of one embodiment of an expansion tool that can be used to expand the joint prosthesis of FIGS. 19-20.

For example, an expansion tool 2160 shown in FIG. 21 can be used to expand the segments 1954 of the joint implant component 1900 from a first configuration to an expanded configuration, wherein the diameter of the central opening 1958 of the post portion 1948 is increased in the expanded configuration with respect to the diameter of the central opening 1958 in the first configuration.

Figure 22:
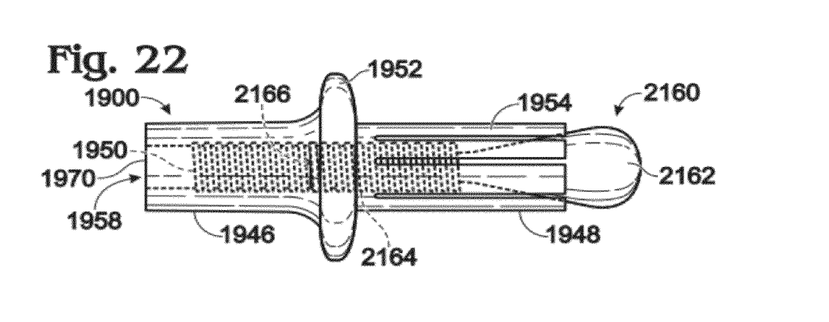
FIG. 22 is an elevation view of the expansion tool of FIG. 21 in place within a joint prosthesis.

One embodiment of an expansion tool 2160 can comprise a tapered portion 2162, a threaded portion 2164, and an internal opening 2166 configured to engage with, for example, a screwdriver head 2168. The expansion tool 2160 can be inserted into the implant component 1900 such that the threaded portion 2164 of the expansion tool 2160 engages with the internal threads 1950 of the implant component 1900. FIG. 22 shows the expansion tool 2160 positioned at least partially inside the central opening 1958 of the implant component 1900. As shown in FIG. 22, at least a portion of the tapered portion 2162 of the expansion tool 2160 can be positioned inside the central opening 1958 of the post portion 1948 of the implant component 1900 (e.g., inside the segments 1954).

In order to expand the post portion 1948 of the implant component (e.g., in order to move the segments 1954 radially outward and increase the gap between the segments), a screwdriver head 2168 or other tool can be inserted through the central opening 1958 at the end 1970 adjacent the taper portion 1946 of the implant component 1900. The screwdriver head 2168 can engage with the expansion tool 2160 via the internal opening 2166. Turning the screwdriver head 2168 can cause the expansion tool 2160 to be drawn through the central opening 1958 of the implant component 1900, in a longitudinal direction towards the end 1970 adjacent the taper portion 1946, due to engagement of the threaded portion 2164 of the expansion tool 2160 with the internal threads 1950 of the implant component 1900. As the expansion tool 2160 is pulled through the segments 1954, the segments 1954 are forced radially outward by the tapered portion 2162 of the expansion tool 2160.

Figure 23:
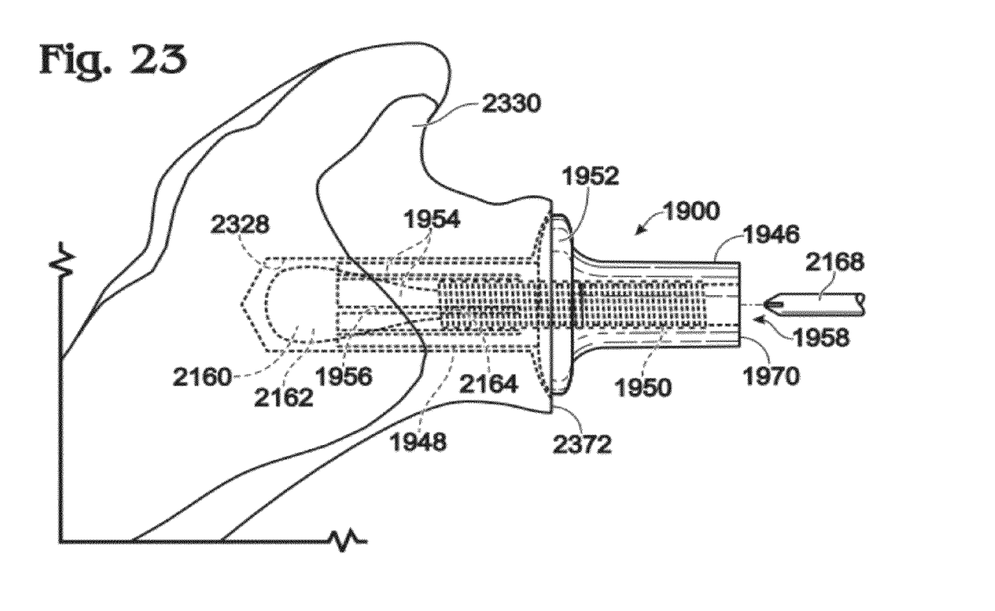
FIG. 23 is an elevation view of a joint prosthesis implanted within a patient's bone.
Figure 24:
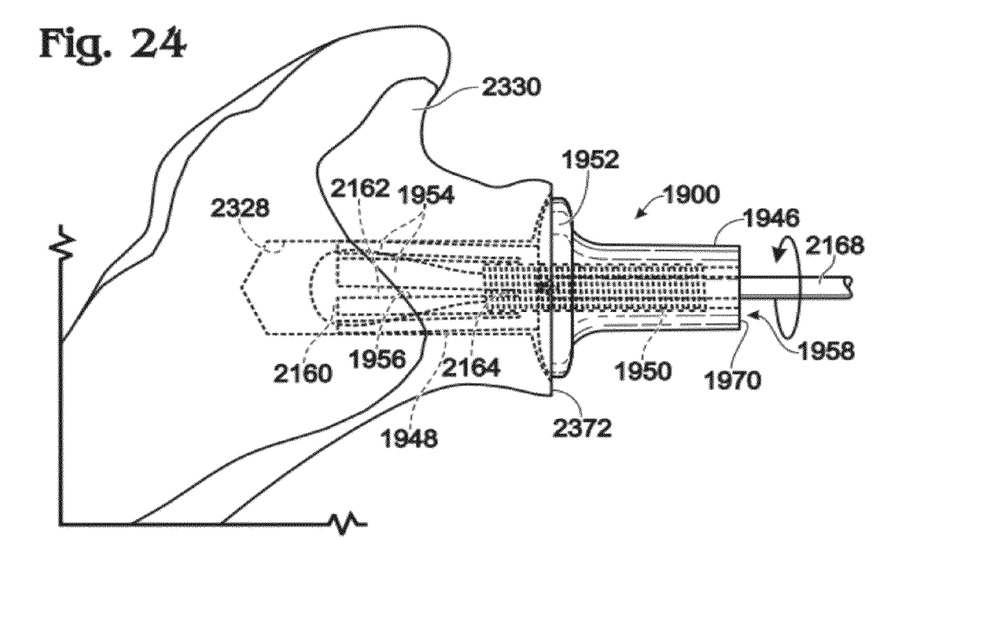
FIG. 24 is an elevation view of the joint prosthesis of FIG. 23, after partial expansion of the prosthesis.

FIGS. 23-24 further illustrate expansion of an implant component 1900 in place within a patient's bone 2330 (e.g., femur 2330). A hole 2328 can be drilled into a patient's bone 2330 and sized such that the post portion 1948 of the implant component 1900 can be inserted into the hole 2328 by hand in some embodiments. When inserted, at least a portion of the post portion 1948 of the implant component 1900 can be positioned within a hole 2328 drilled into a patient's bone 2330. In some embodiments, the annular portion 1952 can rest against a surface 2372 of bone 2330. Annular portion 1952 can be enlarged so as to prevent insertion of the taper portion 1946 in the hole 2328 (e.g., the annular portion 1952 can serve as a stopper, preventing the implant 1900 from being inserted too far into a patient's bone 2330).

The expansion tool 2160 can be positioned within the central opening 1958 of the implant component 1900 before the post portion 1948 is inserted into the hole 2328 in the patient's bone 2330. In this manner, once the post portion 1948 is inserted into the bone 2330, a screwdriver head 2168 can be inserted through the end 1970 adjacent the taper portion 1946 (e.g., the portion of the implant component 1900 that is arranged outside of the bone 2330). The screwdriver head 2168 can engage with the internal opening 2166 of the expansion tool, and as the screwdriver head 2168 is turned (FIG. 24), the expansion tool 2160 can be drawn through the central opening 1958 of the implant component 1900, towards the end 1970 of the taper portion 1946. As the expansion tool 2160 is drawn through the segments 1954 of the post portion 1948, the segments 1954 are moved radially outward, increasing the size of the longitudinal slits 1956 (e.g., the gap) between adjacent segments 1954, thereby increasing the diameter of the central opening 1958 within the post portion 1948 and increasing the frictional engagement or press fit of the post portion 1948 with the patient's bone 2330.

Figure 25:
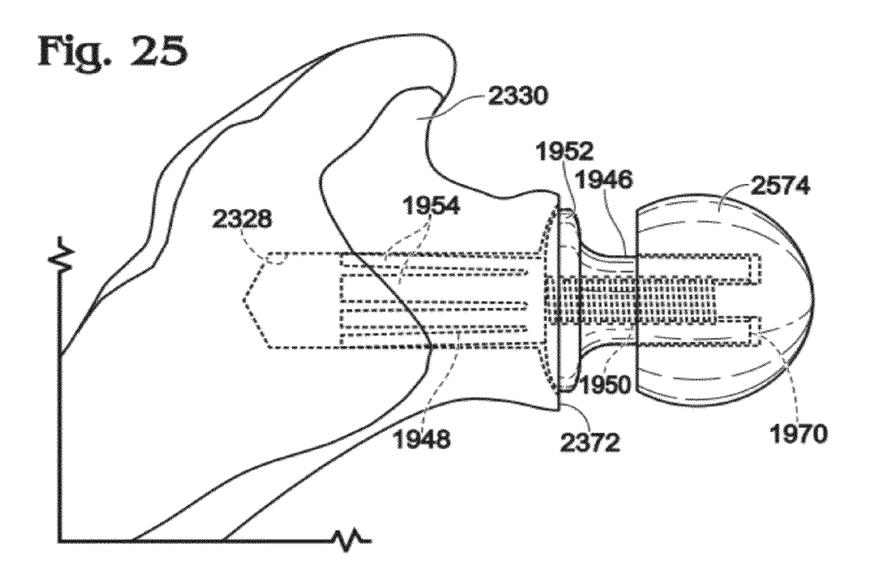
FIG. 25 is an elevation view of an expanded joint prosthesis implanted into a patient's bone.

As shown in FIG. 25, the expansion tool can be drawn entirely through the implant component 1900, leaving the expanded implant component 1900 in the hole 2328 of the bone 2330. Once the expansion tool is removed, further procedures can be performed to complete the joint replacement. For example, a second implant component 2574 can be arranged to couple with the implant component 1900. For example, in the specific embodiment shown, a femoral head 2574 (e.g., a cobalt chrome femoral head) can be screwed into the internal threads 1950 within the taper portion 1946 of the implant component 1900. The femoral head 2574 can then engage with one or more additional implant components, such as a prosthetic acetabulum.

Figure 15:
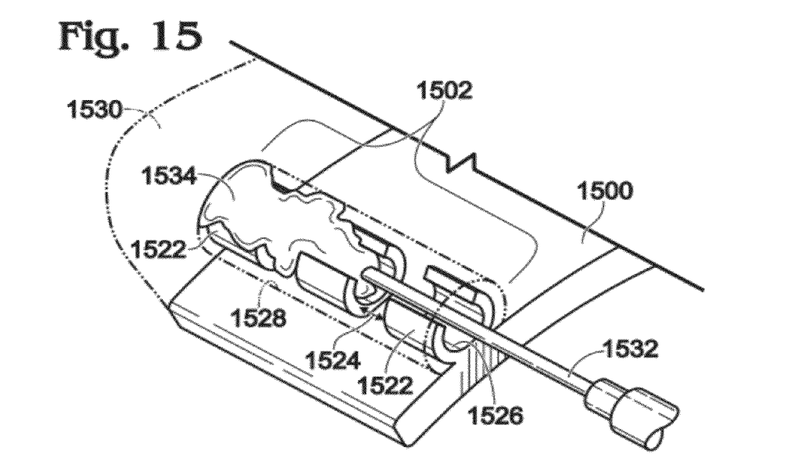
FIG. 15 is a perspective view of cement being implanted into a joint prosthesis according to the present disclosure.

Any of the disclosed embodiments of fixation posts can be configured to receive cement (e.g., polymethylmethacrylate (PMMA), other non-resorbable cements, or a resorbable bone cement) to be injected into the hollow segmented posts. For example, FIG. 15 shows a joint implant component 1500 having at least one hollow segmented fixation post 1502 comprising three segments 1522. A needle 1532 can be inserted into the opening 1526 created by the segments 1522 and cement 1534 can be injected into the central opening 1526 defined by the segments 1522. As shown in FIG. 15, the fixation post 1502 can be configured to allow the cement 1534 to at least partially fill in the opening 1526 and flow out through removed segments of the post 1502 (e.g., flow through the gaps 1524 between adjacent segments 1522). The fixation post 1502 can thereby contribute to fixation of the joint implant component 1500 to a patient's bone 1530 by increasing the press fit engagement with the bone and into the bone (e.g., via expansion of the fixation post), by allowing for the extrusion of bone cement 1534 from the center of the post 1526 into the surrounding bone 1530, and/or by promoting or allowing bone ingrowth through the gaps between adjacent segments and into the fixation post and/or bone ingrowth into porous surface portions on the implant component.

Disclosed embodiments of a hollow segmented fixation post can provide initial fixation (e.g., via press fit engagement with the patient's bone) but also provide the option to inject cement down the center of the post, allowing the cement to flow out through the gaps between adjacent segments of the post, thereby providing a stable localized locking of the implant to the bone. Additionally, disclosed fixation posts can allow for biologic fixation (e.g., bone ingrowth) into and on the joint implant components. For example, in embodiments where cement is not injected into the opening of the fixation posts, bone can grow into the central opening of the fixation posts by growing through the gaps between the segments of the post. In other embodiments (for example, when cement is injected into the central opening), bone ingrowth can develop on, for example, porous surfaces on the joint component and fixation posts. Such bone ingrowth can improve long term fixation of the implant.

Disclosed embodiments of joint prostheses and joint implant components can comprise any suitable metal, plastic, ceramic, coatings, and/or combinations of these. Generally, materials for bearing surfaces of implant components can be selected that provide low-friction movement with minimal generation of wear debris. Specific examples of suitable materials include cobalt chrome alloys, ultra high molecular weight polyethylene (UHMWPE), titanium nitride coatings, molybdenum, titanium, cobalt, and/or alloys or combinations of these materials. Specific examples of surface combinations suitable for articulation with one another include titanium nitride coated metals and UHMWPE, ceramic and ceramic, metal and metal, and other combinations of these.

At least a portion of disclosed embodiments of joint implant components can include porous coatings or treatments, such as PCA beads (Bio-Vac, Inc of Michigan, USA), hydroxy apatite (HA), titanium plasma spray coating, and/or Resorbable Blast Media Coating. In some embodiments, these porous coatings or treatments can promote bone growth in and around the joint implant component.

Methods of replacing at least part of a patient's joint with one or more joint implant components are also disclosed. For example, one method comprises preparing the implant site to receive the one or more joint implant components and implanting the joint prosthesis wherein at least a portion of the implant component is positioned at least partially within a hole drilled into a patient's bone. Any of the disclosed embodiments of joint implant components can be used in such methods. For example, the joint implant component can comprise a bone-engaging surface and at least one segmented post protruding from the bone-engaging surface, wherein the post comprises at least two segments, each segment being separated by a gap, and wherein the segments define a central opening through the center of said segments.

In some methods, at least one segmented post can be expanded from a first configuration to a second configuration, wherein the diameter of the central opening is increased in the second configuration with respect to the first configuration. For example, an expansion tool, such as the expansion tools shown in FIGS. 18 and 21, can be used to expand one or more segments of the implant component, thereby increasing the press fit of the fixation post within the patient's bone. Thus, in some methods, the at least one segmented post can be expanded by drawing a tapered expansion tool through at least part of the segmented post.

Disclosed methods and joint implant components can provide a surgeon with flexibility as to whether to use biologic fixation or cement fixation for a particular implant component for a particular patient. Such flexibility can be provided without requiring the surgeon to remove the implant or re-prepare the bone surface if he or she decided mid-surgery to alter the fixation approach. For example, a patient's bone can be prepared assuming the implant component will be stabilized using biologic fixation. After preparation and insertion of the implant, the surgeon or other professional can evaluate whether biologic fixation is indeed suitable as the sole fixation method at the time of implantation. If it is determined at the time of implantation that biologic fixation may be insufficient as the sole means of implant fixation, cement can be injected into the central opening of the fixation post, without requiring removal of the implant component.

On the other hand, if a joint implant component was implanted intending to rely on biologic fixation, and a follow-up evaluation a period of time after completion of the joint replacement reveals that the joint prosthesis is insufficiently stable, cement can be injected into the substantially cylindrical opening of one or more of the fixation posts at a date after initial implantation. Such revision surgery may require clearing of fibrous or other growth from within one or more fixation posts in order to re-open the hollow post to accommodate injection of bone cement.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A joint implant component, comprising:
   a bone-engaging surface configured to engage with a patient's bone;
   at least one post protruding outwardly from the bone-engaging surface, to engage with a patient'bone, wherein the post comprises at least two expandable segments, each expandable segment being separated by a gap, and wherein the expandable segments define a central opening through the centers of the expandable segments, wherein the at least one post is positioned transversely to a major axis of the joint implant.

2. A joint implant component, comprising:
   a bone-engaging surface configured to engage with a patient's bone;
   at least one post protruding outwardly from the bone-engaging surface to engage with a patient's bone, wherein the post comprises at least two expandable segments, each expandable segment being separated by a gap, and wherein the expandable segments define a central opening through the centers of the expandable segments, wherein the joint implant comprises at least a first implant member and a second implant member, the first and second implant members being configured to articulate with each other, wherein the first implant member comprises a first bone-engaging surface and the second implant member comprises a second bone-engaging surface, and both the first and second bone-engaging surfaces comprise at least one post protruding from said first and second bone-engaging surfaces.

3. A joint implant component, comprising:
   a post portion configured to engage with a patient's bone, the post portion comprising a plurality of segments arranged around the circumference of the post portion and spaced apart by a plurality of longitudinal slits extending along at least a portion of the length of the post portion; and
   a taper portion coupled to the post portion and having a threaded inner wall, wherein the post portion and taper portion are arranged such that a longitudinal central opening extends through the post portion and taper portion, wherein the segments of the post portion are expandable from a first configuration to an expanded configuration, wherein at least a part of the post portion has a porous surface.

4. The joint implant component according to claim 3, wherein the segments are positioned relative to one another such that they are configured to receive a cement injection needle within the central opening.

5. The joint implant component according to claim 3, wherein the diameter of the central opening is increased in the expanded configuration with respect to the first configuration.

6. The joint implant component according to claim 3, wherein the joint implant component is a femoral hip stem.

7. The joint implant component according to claim 3, further comprising a curved annular portion positioned between the taper portion and the post portion, wherein the curved annular portion is configured to engage with a surface of a patient's bone.

* * * * *